United States Patent [19]

McGregor

[11] 4,110,104

[45] Aug. 29, 1978

[54] HERBICIDAL USE OF AMINOHALOPYRIDYLOXY ACIDS AND DERIVATIVES THEREOF

[75] Inventor: Stanley D. McGregor, Midland, Mich.

[73] Assignee: The Dow Chemical Company, Midland, Mich.

[21] Appl. No.: 753,753

[22] Filed: Dec. 23, 1976

Related U.S. Application Data

[60] Continuation-in-part of Ser. No. 342,783, Mar. 19, 1973, abandoned, which is a division of Ser. No. 166,257, Jul. 26, 1971, Pat. No. 3,761,486.

[51] Int. Cl.$^2$ .............................................. A01N 9/22
[52] U.S. Cl. ..................................................... 71/94
[58] Field of Search ............................................ 71/94

[56] References Cited

U.S. PATENT DOCUMENTS

| | | | |
|---|---|---|---|
| 2,341,868 | 2/1944 | Hitchcock et al. | 71/109 |
| 2,577,969 | 12/1951 | Jones | 71/109 |
| 3,276,856 | 10/1966 | Esposito | 71/94 |
| 3,285,925 | 11/1966 | Johnston et al. | 71/94 |
| 3,317,542 | 5/1967 | Haszeldine et al. | 71/94 |
| 3,317,549 | 5/1967 | Johnston | 71/94 |
| 3,483,246 | 12/1969 | Kaufman | 71/94 |
| 3,489,761 | 1/1970 | Kaver | 71/94 |
| 3,753,678 | 8/1973 | Young et al. | 71/94 |
| 3,883,541 | 5/1975 | Hamilton | 71/94 |

OTHER PUBLICATIONS

Cava et al., "Pyridine Ders. II, Some Halogen, etc.", (1958), J. Org. Chem. 23, pp. 1614–1616, (1958).
Veldstra, "Form and Function of Plant Growth Avk.", (1955), CA53, pp. 18199, (1959).

Primary Examiner—Glennon H. Hollrah
Attorney, Agent, or Firm—S. Preston Jones; C. Kenneth Bjork

[57] ABSTRACT

Compounds corresponding to the formula

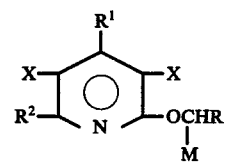

wherein X represents chloro, bromo, or fluoro; R represents one of cyano (-CN), carbamoyl (—CONR$^3$R$^4$) or carboxy (—COOH) or the carboxylic acid salts thereof; each of R$^3$ and R$^4$ independently represents hydrogen or alkyl of 1 to 8 carbon atoms; M represents hydrogen or loweralkyl; R$^1$ represents hydrogen, loweralkyl, amino or loweralkylamino of 1 to 4 carbon atoms; and R$^2$ represents hydrogen, X, loweralkyl, amino or loweralkylamino, with the proviso that one of R$^1$ or R$^2$ is always amino or loweralkylamino and the other of R$^1$ and R$^2$ is always other than amino or loweralkylamino are prepared. These compounds are useful as herbicides and as active agents in compositions used as herbicides.

6 Claims, No Drawings

HERBICIDAL USE OF AMINOHALOPYRIDYLOXY ACIDS AND DERIVATIVES THEREOF

CROSS-REFERENCE TO RELATED APPLICATIONS

This is a continuation-in-part of Application Ser. No. 342,783 filed March 19, 1973 now abandoned, which in turn is a division of application Ser. No. 166,257 filed July 26, 1971, now U.S. Pat. No. 3,761,486, issued Sept. 25, 1973.

SUMMARY OF THE INVENTION

The present invention is directed to novel compounds corresponding to the formula

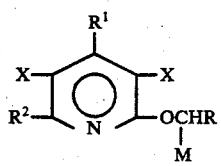

In this and succeeding formulae, wherein X represents chloro, bromo, or fluoro; R represents one of cyano (—CN), carbamoyl (—CONR$^3$R$^4$) or carboxy (—COOH) or the carboxylic acid salts thereof; each R$^3$ and R$^4$ independently represents hydrogen or alkyl of 1 to 8 carbon atoms; M represents hydrogen or loweralkyl; R$^1$ represents hydrogen, loweralkyl of 1 to 4 carbon atoms, amino or loweralkylamino of 1 to 4 carbon atoms; and R$^2$ represents hydrogen, X, loweralkyl, amino or loweralkylamino, with the proviso that one of R$^1$ or R$^2$ is always amino or loweralkylamino and the other of R$^1$ and R$^2$ is always other than amino or loweralkylamino.

In the present specification and claims, the term "loweralkyl" is employed to designate a straight, branched or cyclic alkyl radical containing from 1 to 4 carbon atoms.

In the present specfication and claims, the term "loweralkylamino" as employed designates either straight, branched chain or cyclic mono- or dialkyl- amino radicals wherein each alkyl group contains from 1 to 4 carbon atoms.

The present invention also is understood to encompass compounds wherein all the "X" substituents are the same as well as those wherein different halogens are present in the same compound.

The term "salt" as employed in the present specification and claims designates the reaction products of basic compounds with the acid functional group —COOH. Such salts can be represented by the formula —COOMe wherein Me represents ammonium, the alkali metals such as sodium, lithium, potassium, cesium or rubidium, the alkaline earth metals such as calcium, barium and strontium and the heavy metals including antimony, zinc, bismuth, cadmium, cerium, chromium, cobalt, copper and other metals having a density of above 4.

The present invention is also directed to plant husbandry and the raising of crops and is concerned with an agronomical practice and composition for improving the emergence, seed germination, seedling growth and harvest of crop plants. This invention also relates to herbicidal compositions and to methods of inhibiting or controlling undesirable plant growth therewith in the presence of important economic crops.

The active compounds of the present invention are crystalline solids or oils which are moderately soluble in common organic solvents.

The 2-substituted aminohalopyridines of the present invention are prepared by a variety of methods. Those compounds wherein R is carboxy (—COOH), are prepared by the hydrolysis of the corresponding alkyl ester. This reaction can be exemplified as follows:

Reaction I

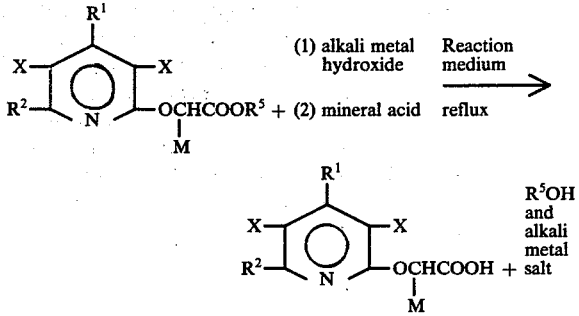

wherein R$^1$, R$^2$, X and M are as hereinbefore defined and R$^5$ represents an alkyl radical of from 1 to 12 carbon atoms.

In carrying out this reaction, the ester reactant in a reaction medium or solvent is treated, under reflux conditions, with an alkali metal hydroxide for a period of time of from about 0.5 to about 3 hours. Thereafter, the reaction product is acidified with a mineral acid and the desired product recovered by filtration or other conventional separatory procedures.

The reaction consumes the reactants in stoichiometric proportions, i.e. one equivalent of the ester reactant per equivalent of the alkali metal hydroxide and mineral acid. However, due to the nature of the hydrolysis reaction, it is preferred that a slight excess of the alkali metal hydroxide and mineral acid be employed. If desired, the product can be purified by recrystallization from a solvent such as, for example, nitromethane, carbon tetrachloride, n-hexane, cyclohexane, chloroform, benzene, methanol, ethanol or a methanol-water mixture or by the use of a combination of any of these solvents and/or by the sequential use of one or more of these solvents.

Representative reaction mediums, i.e. solvents for carrying out the reaction include, for example, water, dioxane, dimethylformamide, dimethylsulfoxide, tetrahydrofuran and other conventional ether solvents. Representative alkali metal hydroxides for use as reactants are the hydroxides of sodium, potassium, cesium, lithium and rubidium.

The compounds of the present invention wherein R is carboxylic acid salts (—COOMe) can be prepared by the reaction of the appropriate aminohalopyridyloxy carboxylic acid with appropriate metal hydroxide or carbonate. In carrying out the reaction, substantially equivalent proportions of the acid and base are mixed together in a suitable solvent such as an alcohol-water mixture whereupon a reaction takes place with the formation of the desired salt product and water-byproduct. The salt may or may not be soluble in the reaction medium. If insoluble, it may be recovered by filtration; if soluble, it may be recovered by vaporizing off the solvent and water. The salt may be purified, if desired, by conventional methods.

Salts of metals which form difficultly soluble hydroxides, such as, for example, copper, may be prepared by an alternative procedure wherein an alkali metal salt of the desired compound is reacted with a soluble mineral acid salt of said metal, such as the chloride or nitrate to produce the said metal salts of acid compound. In such preparation, substantially equivalent proportions of the alkali metal salt compound and said metal salt of a mineral acid are stirred together in water or a water-alcohol solvent at room temperature or with gentle warming for from 0.5 to several hours whereupon the desired metal salt compound usually precipitates in the reaction mixture. The latter may be recovered by filtration and purified, if desired, by conventional procedures.

The compounds wherein R is carbamoyl (—CONR$^3$R$^4$) can be prepared by the direct amination of the corresponding carboxylic acid alkyl ester compound with ammonia or an amine. The reaction can be exemplified as follows:

Reaction II

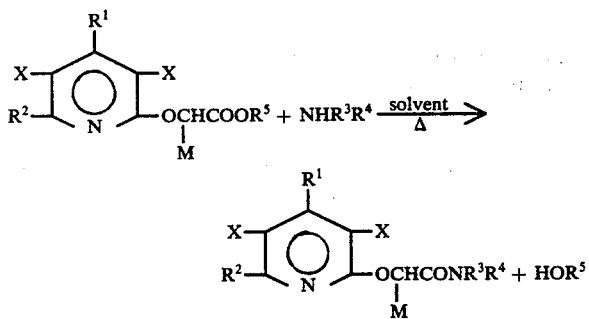

wherein each of R$^1$, R$^2$, R$^3$, R$^4$, R$^5$, X and M are as hereinbefore defined.

In carrying out the reaction, the ester and ammonia or amine reactants in a solvent or reaction medium are contacted together in any suitable fashion and maintained together, under agitation, for a period of time of from about 1 to about 20 hours. When one of the reactants is a highly volatile material, it is preferred that a closed reaction vessel be employed to prevent loss of this reactant. The reaction can be carried out at a temperature of from about room temperature to about 100° C. Upon completion of the reaction, the excess ammonia or amine reactant is removed by flashing or evaporation under reduced pressure. The solid material is thereafter recrystallized from solvents listed hereinbefore.

The compounds wherein R is carbamoyl can also be prepared by the reaction of (A) a 2-(hydrocarbylsulfonyl)aminohalopyridine compound corresponding to the formula

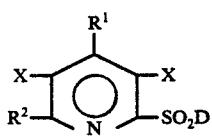

wherein R$^2$ and X are as hereinbefore defined; R$^1$ is other than chloro, bromo or fluoro and D is a straight or branched chain alkyl radical of 1 to 12 carbon atoms or phenyl, with (B) an alkali metal amide salt corresponding to the formula

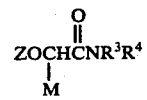

wherein R$^3$, R$^4$ and M are as hereinbefore defined and Z is sodium, lithium, potassium, cesium or rubidium. The alkali metal amide salt can be either prepared in situ as a part of the process or it may be a pre-formed material.

The reaction is initiated by contacting the reactants together with agitation in the presence of a reaction medium, such as one of those listed hereinbefore for a period of from about 0.5 to about 4 hours. The reaction is carried at a temperature in the range of from about 25° to about 100° C. The reaction consumes the reactants in stoichiometric proportions, i.e., one equivalent of the pyridine reactant per equivalent of the alkali metal amide salt reactant. However, due to the nature of the reaction, it is preferred that a slight excess of the alkali metal amide salt reactant be employed. The reaction mixture is usually diluted with water and extracted with a solvent such as, for example, methylene chloride, ether, benzene or chloroform. The extract is dried, if desired, and the solvent removed by conventional techniques and as, for example, evaporation under reduced pressure. The product can be purified by recrystallization from a solvent such as one of those listed hereinbefore.

A convenient method of preparing the alkali metal amide salt reactant in situ, is to react an alkali metal hydride as a mineral oil dispersion in the reaction medium with an amide corresponding to the formula

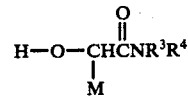

wherein M, R$^3$ and R$^4$ are as hereinbefore defined. In this reaction, the temperature is kept below about 15° C. and the reactants are maintained under constant agitation until the reaction is complete, usually a period of from about 15 to 45 minutes. Thereafter, the pyridine reactant is added and the remaining reaction carried out as hereinabove described.

DESCRIPTION OF SOME PREFERRED EMBODIMENTS

The following examples illustrate the present invention and the manner by which it can be practiced but, as such, should not be construed as limitations upon the overall scope of the same.

EXAMPLE I

4-Amino-3,5-dichloro-2-(pyridyloxy)acetic acid:ethyl ester

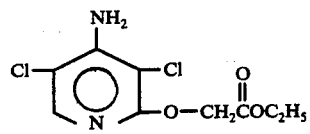

To a flask containing 250 milliliters of tetrahydrofuran under a nitrogen atmosphere was added 5.3 grams (0.2 mole) of sodium hydride as a 50 percent dispersion in mineral oil. To this solution is added 11.5 grams (0.13 mole) of methyl glycolate. The mixture was maintained at a temperature of below 15° C. Thereafter, 24.1 grams (0.1 mole) of 4-amino-3,5-dichloro-2-(methylsulfonyl)-pyridine was added thereto. The mixture was maintained under reflux conditions for 1.5 hours. The mixture was cooled to room temperature and poured into water and extracted with methylene chloride. The extract was dried and the solvent removed by evaporation under reduced pressure. The solid residue which remained was recrystallized from methanol. The 4-amino-3,5-dichloro-2-(pyridyloxy)acetic acid:ethyl ester product had a melting point of 116°–117° C.

EXAMPLE II

2-[4-Amino-3,5,6-trichloro-2-(pyridyloxy)]propionic acid:ethyl ester

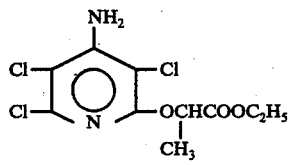

A solution of 21.4 grams (0.1 mole) of 4-amino-3,5,6-2-pyridinol in 100 milliliters of dimethylformamide was added dropwise to 4.8 grams (0.1 mole) of sodium hydride as a 50 percent dispersion in mineral which was slurried in 150 milliliters of dimethylformamide, under nitrogen. The temperature rose to 39° C. and the mixture was maintained under agitation for 20 minutes. Thereafter 18.1 grams (0.1 mole) of ethyl bromopropionate was added over a 10-minute period and the solution was heated for 1 hour over a temperature range of 60° to 80° C. The reaction mixture was cooled, poured into ice water and extracted with methylene chloride. The methylene chloride was evaporated and the 2-[4-amino-3,5,6-trichloro-2-(pyridyloxy)]propionic acid:ethyl ester product recovered had a molecular weight of ~313.

EXAMPLE III

2-[4-(Methylamino)-(3,5-dichloro-6-fluoro-2-pyridyloxy)]propionic acid:ethyl ester

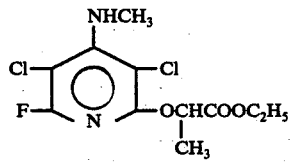

A mixture comprising 10.65 grams (0.05 mole) of 3,5-dichloro-2,6-difluoro-4-(methylamino)pyridine, 7.28 grams (0.07 mole) of ethyl glycolate and 150 milliliters of dry p-dioxane. To the mixture was added a dioxane slurry containing 3.6 grams (0.075 mole) of hexane washed sodium hydride (as a 50 percent oil dispersion). The mixture foamed and when foaming ceased, the mixture was heated under reflux (~100° C.) for 2 hours. At the end of this period, the reaction mixture was poured into ice water and extracted 3 times with 100 milliliter portions of dichloromethane. The extracts were combined, dried, and filtered and thereafter concentrated under reduced pressure. The 2-[4-(methylamino)-(3,5-dichloro-6-fluoro-2-pyridyloxy)]propionic acid:ethyl ester product was recovered in a yield of 15 grams of a yellow oil. The product, in the form of a solid, was recovered by dissolving the oil in 100 milliliters of methylcyclohexane in a glass container and scratching the side of the container with a glass rod to precipitate the product. The product, melted at 67°–68.5° C. and upon analysis, was found to have carbon, hydrogen and nitrogen contents of 42.61, 4.23 and 8.91 percent, respectively, as compared with the theoretical contents of 42.46, 4.21 and 9.0 percent, respectively, calculated for the above-named structure.

EXAMPLE IV

2-[4-Amino-3,5,6-trichloro-2-(pyridyloxy)]propionic acid

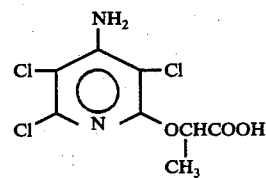

A mixture of 18.0 grams (0.6 mole) of 2-[4-amino-3,5,6-trichloro-2-(pyridyloxy)]propionic acid:ethyl ester, prepared as in Example II and 3.0 grams (0.08 mole) of sodium hydroxide dissolved in 150 milliliters of water was heated, with agitation, at 95° C. for 2 hours. The reaction mixture was cooled to room temperature and the 2-[4-amino-3,5,6-trichloro-2-(pyridyloxy)]propionic acid product was precipitated therefrom by acidification with dilute hydrochloric acid. The product was recovered in a yield of 62 percent of theoretical by filtration and melted at 186°–187° C.

EXAMPLE V

2-[4-Amino-3,5-dichloro-2-(pyridyloxy)]propionamide

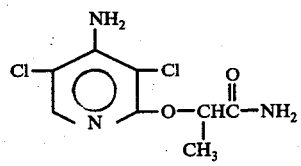

To a flask containing 20 milliliters of tetrahydrofuran was added 9.6 grams of a 50 percent sodium hydride in mineral oil dispersion. Thereafter 17.9 grams of lactamide (HO(CH$_3$)CHCONH$_2$) in 150 milliliters of tetrahydrofuran was added thereto, with agitation, while the mixture was maintained at about 5° C. for about 0.5 hour. To this mixture is added 45 grams of 4-amino-3,5-dichloro-2-(methylsulfonyl)pyridine and the mixture heated and refluxed for a total of 1.5 hours. The mixture was cooled and diluted with water and extracted with methylene chloride. The extract was washed with water, dried and the solvent removed by evaporation under reduced pressure. The crude 2-[4-amino-3,5-dichloro-2-(pyridyloxy)]propionamide which remained was purified by recrystallization from nitromethane and recovered in a yield of 38.1 percent yield and melted at 146.5°–148° C.

EXAMPLE VI

4-Amino-3,5-dichloro-2-(pyridyloxy)acetamide

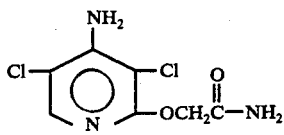

To a 75 milliliter stainless steel bomb is added 15 grams (0.06 mole) of 4-amino-3,5-dichloro-2-(pyridyloxy)acetic acid:ethyl ester, prepared as in Example I. The bomb was cooled to about minus 70° C. in a dry ice bath and thereafter 7 grams (0.04 mole) of ammonia was distilled into the bomb. The bomb was sealed and allowed to stand at room temperature for 48 hours. The bomb was opened and the unreacted ammonia allowed to escape. The solid residue which remained was removed from the bomb and recrystallized from 250 milliliters of ethanol. The 4-amino-3,5-dichloro-2-(pyridyloxy)acetamide product was dried azeotropically with benzene and was recovered in a yield of 72 percent of theoretical and melted at 192°–193° C.

EXAMPLE VII

4-Amino-3,5-dichloro-2-(pyridyloxy)acetic acid

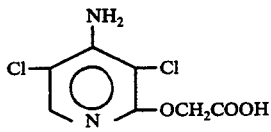

To a solution containing 5 milliliters of 5N sodium hydroxide, 45 milliliters of water and 50 milliliters of dioxane was added 4.9 grams of 4-amino-3,5-dichloro-2-(pyridyloxy)acetic acid:butyl ester. The mixture was boiled for 0.5 hour and thereafter acidified with dilute hydrochloric acid and cooled to room temperature. The 4-amino-3,5-dichloro-2-(pyridyloxy)acetic acid which precipitated was recovered in an equimolar yield by filtration and melted at 200°–201° C. By elemental analysis, the product was found to have carbon, hydrogen and nitrogen contents of 35.65, 2.47 and 11.77 percent, respectively, as compared to the theoretical contents of 35.46, 2.55 and 11.82 percent, respectively, calculated for the above-named compound.

EXAMPLE VIII

2-[4-(Methylamino)-3,5-dichloro-6-fluoro-2-(pyridyloxy)]propionic acid

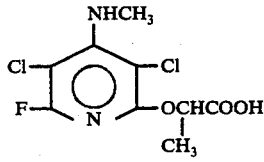

A solution was prepared by dissolving 6.22 grams (0.02 mole) of 2-[(3,5-dichloro-6-fluoro-4-(methylamino)-2-(pyridyloxy)]propionic acid:ethyl ester in 50 milliliters of ethanol. To this solution was added a solution prepared by dissolving 1.6 grams (0.04 mole) of sodium hydroxide in 25 milliliters of water. The mixture was warmed to 55° C. and then allowed to cool to room temperature. The cooled solution was poured onto crushed ice and acidified with hydrochloric acid. The 2-[(4-(methylamino)-3,5-dichloro-6-fluoro-2-(pyridyloxy))]propionic acid product was recovered as a white precipitate by filtration and dried overnight in a vacuum oven at 50° C. and 30 milliliters of mercury. The product was recovered in a yield of 5.5 grams and after recrystallization from hot toluene melted at 172°–173° C. Upon analysis, the product was found to have carbon, hydrogen and nitrogen contents of 38.22, 3.17 and 9.69 percent, respectively, as compared with the theoretical contents of 38.19, 3.21 and 9.90 percent, respectively, calculated for the above-named compound.

The following compounds of the present invention are prepared in accordance with the methods hereinbefore set forth.

N-Butyl 4-amino-3,5-dichloro-2-(pyridyloxy)acetamide having a melting point of 122°–123° C.;

2-[4-Amino-3,5-dichloro-6-fluoro-2-(pyridyloxy)]propionic acid having a melting point of 186°–188° C.;

2-[4-Amino-6-bromo-3,5-dichloro-2-(pyridyloxy)]acetic acid having a molecular weight of 315.91;

N,N-dimethyl 2-[4-amino-3,5-difluoro-6-methyl-2-(pyridyloxy)]propionamide having a molecular weight of 259.11;

N-Butyl 2-[4-amino-3,5-dichloro-2-(pyridyloxy)]-butyramide having a molecular weight of 320.05;

4-Methylamino-3,5-dichloro-6-fluoro-2-(pyridyloxy)acetic acid having a melting point of 188.5°–189.5° C.

4-Amino-3,5-dichloro-6-fluoro-2-(pyridyloxy)acetic acid having a melting point of 232°–233° C.;

2-[4-Amino-3,5-dichloro-6-fluoro-2-(pyridyloxy)]propionic acid having a melting point of 183°–186° C.;

2-[4-Amino-3,5,6-trifluoro-2-(pyridyloxy)]propionic acid having a molecular weight of 236.15;

N-Octyl[4-amino-3,5-dichloro-2-(pyridyloxy)]acetamide having a melting point of 78°–80° C.;

N,N-Di octyl 6-methylamino-3,5-dibromo-4-n-butyl-2-(pyridyloxy)acetamide having a molecular weight of 619.12;

2-[4-Amino-3,5-dichloro-2-(pyridyloxy)]propionic acid, melting at 156°–157° C.;

2-[4-Ethylamino-3,5-dichloro-6-n-butyl-2-(pyridyloxy)]propionic acid:bismuth salt having a molecular weight of 537.06;

2-[6-Cyclopropylamino-3,5-difluoro-2-(pyridyloxy)]hexanoic acid having a molecular weight of 204.06;

2-[4-Isopropylamino-3,5,6-trifluoro-2-(pyridyloxy)]butyramide having a molecular weight of 291.12;

4-Dimethylamino-3,5-dichloro-6-ethyl-2-(pyridyloxy)acetonitrile having a molecular weight of 260.02;

2-[4-Amino-3,5,6-trifluoro-2-(pyridyloxy)]propionic acid having a molecular weight of 236.08;

N-methyl 4-amino-3,5-dichloro-2-(pyridyloxy)acetamide having a melting point of 146°–148° C.;

6-Amino-3,5-dichloro-2-(pyridyloxy)acetic acid having a molecular weight of 236.99;

6-Amino-3,5-dichloro-2-(pyridyloxy)acetic acid:sodium salt having a molecular weight of 258.98;

2-[6-Dibutylamino-3,5-dichloro-4-methyl-2-(pyridyloxy)]propionic acid:copper salt having a molecular weight of 439.63;

4-Butylamino-3,5-dibromo-2-(pyridyloxy)acetic acid:calcium salt having a molecular weight of 415.03; and 2-[4-(Methylamino)-3,5,6-trichloro-2-(pyridyloxy)]-propionic acid:potassium salt decomposing at 220° C.

In accordance with the present invention, it has been discovered that the substituted aminohalopyridines of the present invention are useful as herbicides. In accordance with this invention, a method for controlling or inhibiting the growth of undesirable plant species is provided which comprises applying to plants, plant parts or their habitat, an effective or growth inhibiting amount of at least one of the substituted aminohalopyridines as set forth hereinabove.

An outstanding feature of the present invention is the ability of the compounds to control, either by post-emergent or pre-emergent application, the growth of small seeded grasses and broadleaf plants, such as, for example, barnyard grass, crabgrass, yellow foxtail, Johnson grass, wild oats, bindweed, pigweed, ragweed and wild mustard. This ability is of utmost importance since the compounds are not usually harmful to economical, large seeded crop plants, such as, for example, corn, rice, soybeans or wheat. This feature allows for selective control of the undesirable small seeded plants in the presence of the economical large seeded crop plants.

The application of the compounds of the present invention to plants and plant parts and their habitats, gives rise to varying degrees of response to the compounds depending upon the nature of the plant or seed, the stage of growth or maturity of the plant, the specific compound employed, and the dosage at which plant or plant part or habitat exposure to the compound is carried out, as well as environmental conditions. When large dosages of many of the compounds are applied to the foliage of undesirable plants, a substantially complete kill is obtained. Soil or foliar applications of more dilute dosages of many of the compounds suppress the growth of the germinant seeds and seedlings of many undesirable grasses while having little or no effect upon the seeds, emerging seedlings of established plants of many desirable crop plants. Thus, many of the compounds can be employed for the selective control of emerging seedlings of undesirable weeds in plants or stands of desirable crop plants.

The minimum amount of active compound applied should be that which is effective in controlling and/or killing undesirable plant growth. Ordinarily, for pre-emergent control, good results are obtained when from 0.01 to 50 pounds or more of at least one of the active substituted aminohalopyridine compounds are applied per acre. In foliage treatments, good results are obtained when from 0.1 to 200 pounds of active compound per acre are employed. In selective applications to foliage for the control of many undesirable weeds in the presence of desired crop plants, a uniform dosage of from about 1.0 to 75 pounds of active compound can be employed. In all selective applications, the exact dosage to be employed is depending upon the resistance of the crop plant or their seeds to the pyridine compounds.

The present invention can be carried out by directly employing the pyridine compounds singly or in combination with each other. However, the present invention also embraces the employment of liquid, granular, encapsulated or dust compositions containing at least one of said compounds. In such usage, the compound or compounds can be modified with one or more of a plurality of chemically inert additaments or pesticidal materials including solvents or other liquid carriers, surface active dispersing agents or coarsely or finely divided inert solids. The augmented compositions are also adapted to be employed as concentrates and subsequently diluted with additional inert carrier, to produce other compositions in the form of dusts, sprays, granules, washes or drenches. In compositions where the additament is a coarsely or finely divided solid, a surface active agent and a liquid additament, the added material cooperates with the active component so as to facilitate the invention. Whether the composition is employed in liquid form, as a wettable powder, or as a granular or encapsulated material, the active compound will normally be present in an amount of from about 5 to about 95 percent by weight of the total composition.

In the preapration of dust compositions, the toxicant products can be compounded with any of the finely divided solids, such as, for example, pyrophyllite, talc, chalk, gypsum, fuller's earth, bentonite, attapulgite, and the like. In such operations, the finely divided carrier is ground or mixed with the toxicant or wet with a solution of the toxicant in a volatile organic solvent. Also, such dust compositions when employed as concentrates can be dispersed in water, with or without the aid of dispersing agents to form spray mixtures.

Granular formulations are usually prepared by impregnating a solution of the toxicant in a volatile organic solvent. Also, such dust compositions when employed as concentrates can be dispersed in water, with or without the aid of dispersing agents to form spray mixtures.

Granular formulations are usually prepared by impregnating a solution of the toxicant in a volatile organic solvent onto a bed of coarsely divided clays, such as, for example, attapulgite, bentonite, diatomite, or the like.

Similarly, the toxicant products can be compounded with a suitable water-immiscible organic liquid and a surface active dispersing agent to produce an emulsifiable concentrate which can be further diluted with water and oil to form spray mixtures in the form of oil-in-water emulsions. In such compositions, the carrier comprises an aqueous emulsion, i.e., a mixture of water-immiscible solvent, emulsifying agent and water. Preferred dispersing agents which can be employed in these compositions, are oil-soluble materials including non-ionic emulsifiers such as, for example, the condensation products of alkylene oxides with the inorganic acids, polyoxyethylene derivatives or sorbitan esters, complex ether alcohols and the like. Also, oil-soluble ionic emulsifying agents such as mahogany soaps can be used. Suitable organic liquid which can be employed in the composition include, for example, petroleum oils and distillates, toluene, liquid halohydrocarbons and synthetic organic oils. The surface-active dispersing agents are usually employed in liquid compositions and in the amount of from 0.1 to 20 percent by weight of the combined weight of the dispersing agent and the active compound.

In addition, other liquid compositions containing the desired amount of effective agent can be prepared by dissolving the toxicant in an organic liquid such as, for example, acetone, methylene chloride, chlorobenzene and petroleum distillates. The preferred organic solvent carriers are those which are adapted to accomplish the penetration and impregnation of the environment and particularly soil with the toxicant compounds and are of such volatility as to leave little permanent residue thereon. Particularly desirable carriers are the petroleum distillates boiling almost entirely under 400° F. at atmospheric pressure and having a flash point above 80° F. The proportion of the compounds of this invention employed in a suitable solvent may vary from about 2 to about 50 percent or higher.

In further embodiments, the compounds as employed in accordance with the present invention, or compositions containing the same, can be advantageously employed in the present invention in combination with one or more pesticidal or preservative compounds. In such embodiments the pesticidal or preservative compound is employed either as a supplemental toxicant or as an additament. Representative operable pesticidal or preservative compounds include substituted phenols, cresols, substituted cresols and their metal salts, bisphenols and thiobisphenols; halogenated salicylanilides, organosulfur compounds, carbamate compounds, quaternary ammonium compounds, organometallic compounds, inorganic salts and miscellaneous other compounds, such as phenol, cresol, trichlorophenols, tetrachlorophenols, pentachlorophenol, p-chloro-m-cresol, sodium pentachlorophenol and other sodium, potassium, etc. salts of the phenols, substituted phenols, cresols and substituted cresols, di- and tribrominated salicylanilides, 2,2'-methylenebis(3,4,6-trichlorophenol), 2,2'-thiobis(4,6-dichlorophenoxide), halogenated trifluoromethyl salicylanilide, disodium ethylenebisthiocarbamate, sodium N-methyldithiocarbamate, zinc dimethyldithiocarbamate, 2-mercaptobenzothiazole, 3,5-dimethyltetrahydro-1,3,5-2H-thiadiazine-2-thione, 2,3-dinitro-1,4-dithia-anthraquinone, dodecyl pyridinium chloride, alkyl dimethyl benzyl ammonium chloride, dialkyl dimethylammonium chloride, dialkyl dimethylammonium chloride, bis-tributyltin oxide, bis-tripropyltin oxide, copper pentachlorophenate, copper 8-hydroxyquinolate, sodium borate, 9-undecylenic acid, 10,10-oxybisphenoxarsine, 1-(3-chloroallyl)-3,5,7-triaza-1-azonia-adamantane chloride, 1,4-bromobisacetobutene and substituted phosphorothioates (soil applied insecticides).

In application to an area to be treated, the compounds of this invention may be applied by spraying or by the use of mechanical spreaders in accordance with conventional practice. With respect to application, however, it will be noted that, depending upon the particular circumstances encountered, one method of application may be preferable over others. Thus, for example, for preferred pre-emergence application it has been found very satisfactory to apply the active compound in a liquid spray or on granules and incorporate it into the soil.

In a further method, the distribution can be accomplished by introducing a toxicant or toxicants into the water employed to irrigate the soil. In this method, the amount of water can be varied in accordance with the moisture equivalent or field capacity of the soil in order to obtain the desired depth of distribution of the toxicant.

The following embodiments are illustrative of the present methods.

EXAMPLE IX

Forty-five parts by weight of N-butyl 2-[4-amino-3,5-dichloro-2-(pyridyloxy)]butyramide is mixed and ground with 5 parts by weight of Triton X-155 surfactant (an alkylated aryl polyether alcohol) to prepare a water-dispersible concentrate composition containing 90 percent by weight of the ester compound.

In a further operation, 25 parts by weight of 6-amino-3,5-dichloro-2-(pyridyloxy)acetic acid, 10 parts by weight of Triton X-155 surfactant and 65 parts by weight of xylene are mixed together to prepare an emulsifiable concentrate composition containing 25 percent by weight of said ester compound.

A mixture of 10 parts by weight of 4-dimethylamino-3,5-dichloro-6-ethyl-2-(pyridyloxy)acetonitrile, 10 parts by weight of 2-[4-amino-6-bromo-3,5-dichloro-2-(pyridyloxy)acetic acid, 0.1 part of Nacconol NR detergent (alkyl sulfonate), 0.1 part of Daxad No. 27 (a polymerized sodium salt of benzoid alkyl sulfonic acids) and 200 parts of water are ball-milled together to prepare a water-dispersible liquid concentrate composition containing 20 parts by weight of the mixed pyridine compounds. The concentrate compositions thus prepared can be dispersed in water to prepare aqueous compositions which have very desirable wetting and penetrating properties and are adapted to distribute growth inhibiting amounts of the pyridine compound on plant parts.

EXAMPLE X

In separate operations, aqueous compositions containing substituted aminohalopyridine compounds of the present invention are prepared as follows:

Four parts by weight of one of the pyridine compounds, 0.08 part of sorbitan trioleate (Span 85), and 0.02 part of a sorbitan monoleate polyoxyethylene derivative (Tween 80) are dispersed in 40 milliliters of acetone to produce a concentrate composition in the form of a water-soluble liquid containing one of the ester compounds as the sole active agent. The compounds employed in these procedures including the following:

2-[4-(Methylamino)-3,5,6-trichloro-2-(pyridyloxy)]-propionic acid:potassium salt;

4-Amino-3,5-dichloro-2-(pyridyloxy)acetic acid;

2-[4-Amino-3,5,6-trichloro-2-(pyridyloxy)]-propionic acid;

2-[4-Amino-3,5-dichloro-2-(pyridyloxy)]propionamide;

4-(Methylamino)-3,5-dichloro-6-fluoro-2-(pyridyloxy)acetic acid;

2-[4-Amino-3,5,6-trifluoro-2-(pyridyloxy)]-propionic acid;

4-Amino-3,5-dichloro-2-(pyridyloxy)acetamide;

2-[4-Amino-3,5-dichloro-6-fluoro-2-(pyridyloxy)]-propionic acid;

4-Amino-6-bromo-3,5-dichloro-2-(pyridyloxy)acetic acid;

N,N-Dimethyl 2-[4-amino-3,5-difluoro-6-methyl-2-(pyridyloxy)]propionamide;

N-Butyl-2-[4-amino-3,5-dichloro-2-(pyridyloxy)]-butyramide;

N-Octyl 4-amino-3,5-dichloro-2-(pyridyloxy)acetamide;

N,N-Dioctyl 6-methylamino-3,5-dibromo-4-n-butyl-2-(pyridyloxy)acetamide;

2-[4-Amino-3,5-dichloro-2-(pyridyloxy)]propionic acid;

2-[6-Cyclopropylamino-3,5-difluoro-2-(pyridyloxy)]-hexanoic acid;

2-[4-Isopropylamino-3,5,6-trifluoro-2-(pyridyloxy)]-butyramide;

2-[4-Ethylamino-3,5-dichloro-6-n-butyl-2-(pyridyloxy)]propionic acid:bismuth salt;

4-n-Butylamino-3,5-dibromo-2-(pyridyloxy)acetic acid:calcium salt;

6-Amino-3,5-dichloro-2-(pyridyloxy)acetic acid:-sodium salt;

2-[6-Dibutylamino-3,5-dichloro-4-methyl-2-(pyridyloxy)]propionic acid:copper salt;

N-Methyl 4-amino-3,5-dichloro-2-(pyridyloxy)acetamide;

6-Amino-3,5-dichloro-2-(pyridyloxy)acetic acid;

4-Amino-3,5-dichloro-6-fluoro-2-(pyridyloxy)acetic acid;

2-[4-Amino-3,5-dichloro-6-fluoro-2-(pyridyloxy)]propionic acid;

2-[4-(Methylamino)-3,5-dichloro-6-fluoro-2-(pyridyloxy)]propionic acid;

4-Dimethylamino-3,5-dichloro-6-ethyl-2-(pyridyloxy)acetonitrile; and

2-[4-Amino-3,5,6-trifluoro-2-(pyridyloxy)]propionic acid.

Portions of these concentrate compositions are dispersed in separate portions of water to provide aqueous compositions, each containing 0.44 pound of one of the compounds per 100 gallons of ultimate aqueous mixture. The diluted compositions have very desirable wetting and penetrating properties and are adapted to distribute growth inhibiting amounts of the ester compound on plant parts.

EXAMPLE XI

Representative products of the present invention were evaluated for the post-emergent control of barnyard grass, wild mustard, crabgrass, pigweed, yellow foxtail and bindweed. In these evaluations, plots of the above plant species growth to a height of about 4 inches were used. Aqueous spray compositions, each containing 4,000 parts of a given aminohalopyridine compound per million parts of ultimate composition, were prepared in accordance with the procedures of Example X, and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. The results of the examination of the treated plots are set forth below in Table A.

TABLE A

| Compound Employed | Percent Kill and Control of | | | | | |
|---|---|---|---|---|---|---|
| | Barnyard Grass | Wild Mustard | Crabgrass | Pigweed | Yellow Foxtail | Bindweed |
| 4-Amino-3,5-dichloro-2-(pyridyloxy)-acetic acid | 95 | 95 | — | 100 | 95 | 100 |
| 2-[4-Amino-3,5,6-trichloro-2-(pyridyloxy)propionic acid | 95 | 95 | 90 | 100 | 90 | 100 |
| 4-Amino-3,5-dichloro-2-(pyridyloxy)-acetamide | 90 | 100 | 90 | 100 | 90 | 100 |
| 2-[4-Amino-3,5-dichloro-2-(pyridyloxy)]propionamide | 100 | 85 | 100 | 100 | 100 | 100 |
| 2-[4-Amino-3,5-dichloro-2-(pyridyloxy)]propionic acid | 100 | 100 | 100 | 100 | 100 | 100 |
| Control | 0 | 0 | 0 | 0 | 0 | 0 |

EXAMPLE XII

Representative products of the present invention were evaluated for the post-emergent control of barnyard grass, annual morning glory, crabgrass, Jimson weed, yellow foxtail, cocklebur and Johnson Grass. In these evaluations, plots of the above plant species' growth to a height of about 4 inches were used. Aqueous spray compositions, each containing 2,000 parts of a given aminohalopyridyloxy ester compound per million parts of ultimate composition, were prepared in accordance with the procedures of Example X, and each separate composition was applied to a separate plot. The application was made to the point of run-off and was carried out with conventional spraying equipment. Other plots were sprayed with similar compositions containing no toxicant to serve as controls. Thereafter, the plots were maintained under conditions conducive for plant growth. Two weeks after treatment, the plots were examined for plant growth and evaluated. The results of the examination of the treated plots are set forth below in Table B.

TABLE B

| Compound Employed | Percent Kill and Control of | | | | | | |
|---|---|---|---|---|---|---|---|
| | Barnyard Grass | Annual Morning Glory | Crabgrass | Cocklebur | Yellow Foxtail | Johnson Grass | Jimson Weed |
| 2-[4-Methylamino-3,5,6-trichloro-2-(pyridyloxy)]propionic acid:potassium salt | 90 | 90 | 80 | 90 | 70 | 70 | 90 |
| 4-Amino-3,5-dichloro-6-fluoro-2-(pyridyloxy)acetic acid | 0 | 100 | 80 | 100 | 80 | 30 | 100 |
| 4-Methylamino-3,5-dichloro-6-fluoro-2-(pyridyloxy)acetic acid | 0 | 100 | 95 | 100 | 80 | 0 | 100 |
| 2-[4-Methylamino-3,5-dichloro-6-fluoro-2-(pyridyloxy)]propionic acid | 90 | 90 | 90 | 90 | 90 | 100 | 90 |
| 2-[4-Amino-3,5-dichloro-6-fluoro-2-(pyridyloxy)]-propionic acid | 100 | 99 | 100 | 100 | 95 | 100 | 100 |

EXAMPLE XIII

Aqueous compositions of various pyridine compounds prepared in accordance with Example X were employed for pre-emergent applications on plots immediately after they were seeded with crabgrass, wild oats, barnyard grass, wild mustard, pigweed, yellow foxtail and bindweed. Other plots similarly seeded with the above plant species were treated with like compositions containing no toxicant to serve as control plots. The treating applications were carried out by drenching the soil with the aqueous compositions to obtain a treating rate of 20 pounds per acre. Thereafter, the plots were maintained under conditions conducive for good plant growth. Two weeks after treatment, the plots were examined to determine the percent plant growth and evaluated. The results of the examinations are set forth below in Table C.

the crop plant soybeans. The plots were treated with aqueous compositions prepared as set forth in Example X containing the above-named compound as the sole toxicant therein. Other plots similarly seeded with the above-named plant species were treated with aqueous compositions containing no toxicant to serve as control plots. The treating applications were carried out by drenching the soil with the aqueous compositions to obtain a treating rate of one-eight (1/8) pound per acre. Thereafter, the plots were maintained under conditions conducive to good plant growth. Examination of the plots two weeks after treatment showed substantially complete kill and control of all of the weed plant species and profuse growth of soybeans. In the control plots, no

TABLE C

| Compound Employed | Percent Kill and Control of | | | | | | |
|---|---|---|---|---|---|---|---|
| | Barnyard Grass | Wild Mustard | Crab-grass | Pig-weed | Yellow Foxtail | Bind-weed | Wild Oats |
| N-Butyl 4-amino-3,5-dichloro-2-(pyridyloxy)acetamide | 90 | 90 | 100 | 100 | 100 | 90 | — |
| 4-Amino-3,5-dichloro-2-(pyridyloxy)acetic acid | 100 | 100 | 100 | 100 | 100 | 100 | 95 |
| 2-[4-Amino-3,5,6-trichloro-2-(pyridyloxy)]propionic acid | 100 | 100 | 100 | 100 | 100 | 100 | 100 |
| 2-[4-Amino-3,5-dichloro-2-(pyridyloxy)]propionamide | 100 | 100 | 100 | 100 | 100 | 100 | 95 |
| 2-[4-Amino-3,5-dichloro-2-(pyridyloxy)]propionic acid | 100 | 100 | 100 | 100 | 100 | 100 | 100 |
| 4-Amino-3,5-dichloro-2-(pyridyloxy)acetamide | 100 | 100 | 100 | 100 | 100 | 100 | 85 |
| N-Methyl 4-amino-3,5-dichloro-2-(pyridyloxy)acetamide | 80 | 100 | 100 | 100 | 90 | 95 | — |
| Control | 0 | 0 | 0 | 0 | 0 | 0 | 0 |

EXAMPLE XIV

Aqueous compositions of various ester compounds prepared in accordance with Example X were employed for pre-emergent applications on plots immediately after they were seeded with crabgrass, annual morning glory, barnyard grass, Jimson weed, pigweed, yellow foxtail and Johnson grass. Other plots similarly seeded with the above plant species were treated with like compositions containing no toxicant to serve as control plots. The treating application were carried out by drenching the soil with the aqueous compositions to obtain a treating rate of 4 pounds per acre. Thereafter, the plots were maintained under conditions conducive for good plant growth. Two weeks after treatment, the plots were examined to determine the percent plant growth and evaluated. The results of the examinations are set forth below in Table D.

kill or control of any of the plant species could be ascertained.

EXAMPLE XVI

4-Amino-3,5-dichloro-2-(pyridyloxy)acetic acid was evaluated for the selective post-emergent control of Johnson grass, wild mustard, bindweed, barnyard grass, crabgrass and yellow foxtail in plots containing these plant species and wheat plants. In this evaluation, the plants were of a height of about 4 inches. An aqueous spray composition containing 250 parts of the compound per million parts of ultimate composition and prepared in accordance with the procedures of Example X, was applied to a plot containing the above plant species. The application was made to the point of run-off employing conventional spraying equipment. Other plots containing the same plant species were treated with compositions containing no toxicant, to serve as

TABLE D

| Compound Employed | Percent Kill and Control of | | | | | | |
|---|---|---|---|---|---|---|---|
| | Barn-yard Grass | Annual Morning Glory | Crab-grass | Pig-weed | Yellow Foxtail | Johnson Grass | Jimson Weed |
| 4-Amino-3,5-dichloro-6-fluoro-2-(pyridyloxy)acetic acid | 100 | 100 | 100 | 100 | 100 | 100 | 100 |
| 4-Methylamino-3,5-dichloro-6-fluoro-2-(pyridyloxy)acetic acid | 100 | 100 | 100 | 100 | 100 | 99 | 100 |
| 2-[4-Methylamino-3,5-dichloro-6-fluoro-2-(pyridyloxy)]propionic acid | 95 | 80 | 100 | 100 | 95 | 95 | 100 |
| 2-[4-Amino-3,5-dichloro-6-fluoro-2-(pyridyloxy)]propionic acid | 95 | 100 | 100 | 100 | 90 | 95 | 100 |

EXAMPLE XV

4-Amino-3,5-dichloro-2-(pyridyloxy)acetic acid was employed for the selective control of emerging seedlings of the weed plants, crabgrass and wild mustard in plots seeded with the above-named plant species and controls. Thereafter the plots were held for a period of two weeks under conditions conducive for good plant growth. At the end of this period, the plots were examined to determine the degree of kill and control of the plants. In the control plots, all of the plants were growing rapidly and no kill or control of any of the plants could be found. In the acid treated plot, there was substantially complete kill and control of Johnson grass, wild mustard, bindweed, barnyard grass, crabgrass and yellow foxtail and no injury could be found to the wheat plants which were thriving and growing profusely.

The aminohalo-2-pyridyloxy alkanoic acid esters employed as starting materials can be prepared by reacting an appropriate amino-halo-2-pyridinol corresponding to the formula

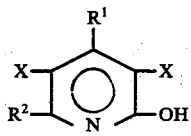

with a halo-substituted loweralkyl ester of acetic acid or propionic acid and corresponding to the formula

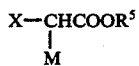

wherein each of $R^1$, $R^2$, $R^5$ and M are as hereinbefore defined, at a temperature in the range of about 25° to about 150° C. for a time of from about 0.5 to about 30 hours in the presence of a solvent such as, for example acetonitrile or p-dioxane and a base such as, for example potassium carbonate or sodium carbonate.

The 4- and 6-amino-(di- or tri-)halo-2-pyridinols employed as starting materials to prepare the esters above, can be prepared by reacting an appropriate 4- or 6-amino-tri- or tetrahalopyridine containing a halogen atom in the 2-position with an aqueous solution of an alkali metal hydroxide at a temperature of from about 120° to about 200° C.

In an alternative procedure, the aminohalo-2-pyridyloxy alkanoic acid esters employed as starting materials can be prepared by the reaction of an aminohalopyridine corresponding to the formula

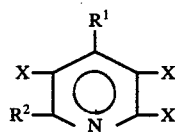

wherein X, $R^1$ and $R^2$ are as hereinbefore defined with an α-hydroxy acetic acid or propionic acid alkyl ester of the formula

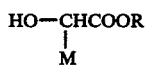

wherein M is as hereinbefore defined and R is alkyl of 1 to 12 carbon atoms.

The reaction is initiated by contacting the reactants together in the presence of a reaction medium or solvent such as, for example, acetonitrile, dimethylformamide, p-dioxane, or dimethylsulfoxide and a base such as, for example, silver carbonate, potassium carbonate, sodium carbonate, sodium hydride or metallic sodium. The reaction is carried out at the reflux temperature of the mixture. The reaction consumes the reactants in stoichiometric proportions, i.e., one equivalent of the pyridine reactant per equivalent of the hydroxy acetic or propionic acid ester reactant. However, due to the nature of the pyridyloxy ester formation, it is preferred that an excess of the hydroxy acetic or propionic acid ester reactant be employed.

The base is employed in amounts ranging from about 1 to about 2 equivalents of base per equivalent of aminohalopyridine reactant.

In carrying out the reaction, the reactants, reaction medium and base are heated to the reflux temperature and maintained at this temperature and in a state of agitation for a period of time of from about 0.5 to about 10 hours or more, until the reaction is complete. The reaction mixture is thereafter cooled, diluted with water and extracted with a solvent such as dichloromethane or other conventional such solvents. The extract is dried, filtered and concentrated by heating under reduced pressure. The product is purified by the trituration with a solvent such as, for example, ether, n-hexane, cyclohexane, pentane or a pentane-ether mixture.

The 2-(hydrocarbylsulfonyl)-4-aminohalopyridines employed as starting materials and corresponding to the formula

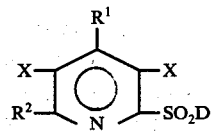

wherein $R^1$, X and D are as hereinbefore defined and $R^2$ is hydrogen, loweralkyl, or X, can be prepared by first reacting an appropriate polyhalopyridine with an appropriate amine at about 50° to about 150° C. and thereafter reacting the so-produced 4-aminohalopyridine compound with sodium metal and an appropriate halocarbylmercaptan in a solvent such as, for example, methanol. The so-produced 2-(hydrocarbylthio)-4-aminohalopyridine is thereafter oxidized to the desired sulfonyl compound by conventional treatment with an oxidizing agent such as, for example, hydrogen peroxide or chlorine water.

The 2-(hydrocarbylsulfonyl)-6-aminodihalopyridines employed as starting materials and corresponding to the formula

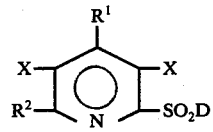

wherein $R^2$, X and D are as hereinbefore defined and $R^1$ is as hereinbefore defined but always other than chloro, bromo or fluoro, can be prepared by the reaction of a 2,3,5,6-tetrahalopyridine with an appropriate amine at temperatures in the range of 50° to 150° C. and thereafter reacting the so-produced 2-aminotrihalopyridine compound with sodium metal and an appropriate hydrocarbylmercaptan in a solvent such as, for example, methanol. The so-produced 2-(hydrocarbylthio)-6-aminodihalopyridine is thereafter oxidized to the desired sulfonyl compound by conventional treatment with an oxidizing agent such as, for example, hydrogen peroxide or chlorine water.

What is claimed is:

1. A method for controlling the growth of undesirable plant species which comprises applying to plants, plant parts or their habitats a herbicidally effective amount of a compound corresponding to the formula

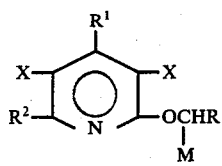

wherein X represents chloro or bromo; R represents carbamoyl (—CONR³R⁴) or carboxy (—COOH) or the carboxylic acid salts thereof; each of R³ and R⁴ independently represents hydrogen or alkyl of 1 to 8 carbon atoms; M represents hydrogen or loweralkyl; R¹ represents hydrogen, loweralkyl, amino or loweralkylamino of 1 to 4 carbon atoms; and R² represents hydrogen, X, loweralkyl, amino or loweralkylamino, with the proviso that one of R¹ or R² is amino or loweralkylamino and the other of R¹ or R² is always other than amino or loweralkylamino.

2. The method of claim 1 wherein the compound is 2-[4-amino-3,5-dichloro-2-(pyridyloxy)]propionic acid.

3. The method of claim 1 wherein the compound is 4-amino-3,5-dichloro-2-(pyridyloxy)acetic acid.

4. The method of claim 1 wherein the compound is 2-[4-amino-3,5,6-trichloro-2-(pyridyloxy)]propionic acid.

5. A composition for the control of undesirable plant growth which comprises as the active agent a herbicidally effective amount of a compound corresponding to the formula

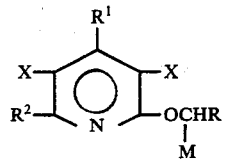

wherein X represents chloro or bromo; R represents carbamoyl (CONR³R⁴) or carboxy (—COOH) or the carboxylic acid salts thereof; each of R³ and R⁴ independently represents hydrogen or alkyl of 1 to 8 carbon atoms; M represents hydrogen or loweralkyl; R¹ represents hydrogen, loweralkyl, amino or loweralkylamino of 1 to 4 carbon atoms; and R² represents hydrogen, X, loweralkyl, amino or loweralkylamino, with the proviso that one of R¹ or R² is always amino or loweralkylamino and the other of R¹ and R² is always other than amino or loweralkylamino in admixture with a chemically inert solid or liquid carrier therefor.

6. The composition of claim 5 wherein the active agent constitutes from about 5 to about 95 percent by weight of the total composition.

* * * * *